United States Patent [19]

Sridhar

[11] Patent Number: 4,828,993
[45] Date of Patent: May 9, 1989

[54] PROCESS FOR THE PREPARATION OF ORGANIC ACIDS

[75] Inventor: Srinivasan Sridhar, Marl, Fed. Rep. of Germany

[73] Assignee: Hüls Aktiengesellschaft, Marl, Fed. Rep. of Germany

[21] Appl. No.: 934,812

[22] Filed: Nov. 25, 1986

[30] Foreign Application Priority Data

Dec. 4, 1985 [DE] Fed. Rep. of Germany ....... 3542861

[51] Int. Cl.$^4$ ........................... C12P 7/40; C12P 7/46
[52] U.S. Cl. ................................. 435/136; 435/145; 204/182.4; 562/580; 562/593
[58] Field of Search .............................. 435/136, 145; 204/182.3, 182.4, 182.5, 182.6, 301; 562/580, 582, 593, 595

[56] References Cited

U.S. PATENT DOCUMENTS 3,391,187  7/1968  Cullen, Jr. et al. ................. 562/580
3,873,425  3/1975  Kobayashi et al. ................. 435/145
3,922,195  11/1975  Chibata et al. ....................... 435/145
3,964,985  6/1976  Giuffrida ........................... 204/182.6
4,734,368  3/1988  Schindler ............................ 435/145

Primary Examiner—Benoit Castel
Assistant Examiner—Rebekah Griffith
Attorney, Agent, or Firm—Oblon, Fisher, Spivak, McClelland & Maier

[57] ABSTRACT

Organic acids are prepared from their salts electrodialytically. At the same time, another acid is converted electrodialytically into the corresponding salt. Both electrodialytic conversions take place in the same electrodialysis unit. If the salt of the organic acid has been fermentatively prepared as, for example, malate from fumarate, it is possible both to prepare malic acid by electrodialysis and also to prepare fumarate from fumaric acid for the fermentation. Through coupling substrate and product streams in the electrodialysis, a closed circuit is formed.

12 Claims, 2 Drawing Sheets

PROCESS FOR THE PREPARATION OF ORGANIC ACIDS

BACKGROUND OF THE INVENTION

1. Field of the Invention

The invention relates to a process for the preparation of organic acids from, for example, Fermentatively prepared salt solutions. Through the use of electrodialysis it is possible to extract the free organic acids and simultaneously to provide the starting substance for the fermentation.

2. Discussion of the Background

For the fermentative conversion of, for example, fumaric acid to L-malic acid, bacteria (German Pat. No. 2,363,285), immobilized bacteria (Europ. J. Appl. Microbiol. 3, 169 (1976)), fungi (German OS 3,310,849), or even immobilized fungi (German OS 2,415,310) may be used. L-malic acid may also be prepared from glucose by means of fungi and bacteria (J. Ferment. Technol. 54, 197 (1976)).

The method of electrodialysis is used in the processing of fermentatively prepared organic acids as early as the fermentation or at a later stage. The objective may be to purify the product or to separate various products from each other or the conversion of the product obtained as a salt into the free acid. The known processes relate to itaconic acid (U.S. Pat. No. 3,873,425), lactic acid (German OS 1,957,395), gluconic acid and glutamic acid. In the process for the preparation of itaconic acid, electrodialysis achieves only a starting-material/product separation and further steps employing ion exchangers are necessary.

Various processes are described for the separation of, for example, L-malic acid from the reaction mixture. Thus, it is proposed to precipitate L-malic acid as the calcium salt (German OS 1,417,033). Fumaric acid is also precipitated at the same time. In this process, losses of materials are unavoidable in the separation of the fumaric acid. Calcium compounds are also needed in this process. A treatment with ion exchangers to convert the salt into the free L-malic acid is also described (German OS 3,247,981). During the regeneration of the ion exchanger, losses of substance inevitably occur. After the regeneration, the eluate represents an environmental pollutant. The use of an additional acid for the regeneration is unavoidable.

By electrodialysis it is also possible to convert a salt of an organic acid (BY) into the free acid ($H_2Y$) using another acid ($H_2X$).

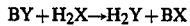

$$BY + H_2X \rightarrow H_2Y + BX$$

In this process a salt (BX) is produced which must be disposed of. The known processes for the processing have the following features:
(1) several process steps (filtering, washing out, dialysis, making up of new solution),
(2) consumption of extraneous substances (calcium salt, acids), and
(3) issue of superfluous streams (wash water, eluates).

SUMMARY OF THE INVENTION

Accordingly, one object of the present invention is to provide an improved and simplified process for the preparation of organic acids from fermentatively prepared salt solutions, in which the material losses are low and in which process starting materials for the fermentation are optionally recovered.

A further object of the invention is to provide a process for the recovery in the acid form of organic acids prepared by fermentation which has the flexibility of being carried out batchwise or by a continuous process.

These objects and other objects of the invention which will become apparent from the following specification have been achieved by the present process for the preparation of a free organic acid from a salt of the organic acid, comprising the steps of (1) converting a salt of the organic acid into the free organic acid by electrodialysis, and (2) forming a second salt from the cation of the salt of the organic acid and the anion of a second acid, wherein the conversion and formation steps are perfomed in the same electrodialysis unit.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings.

DETAILED DESCRIPTION OF THE PREFERRED EMBODIMENTS

Figure 1:
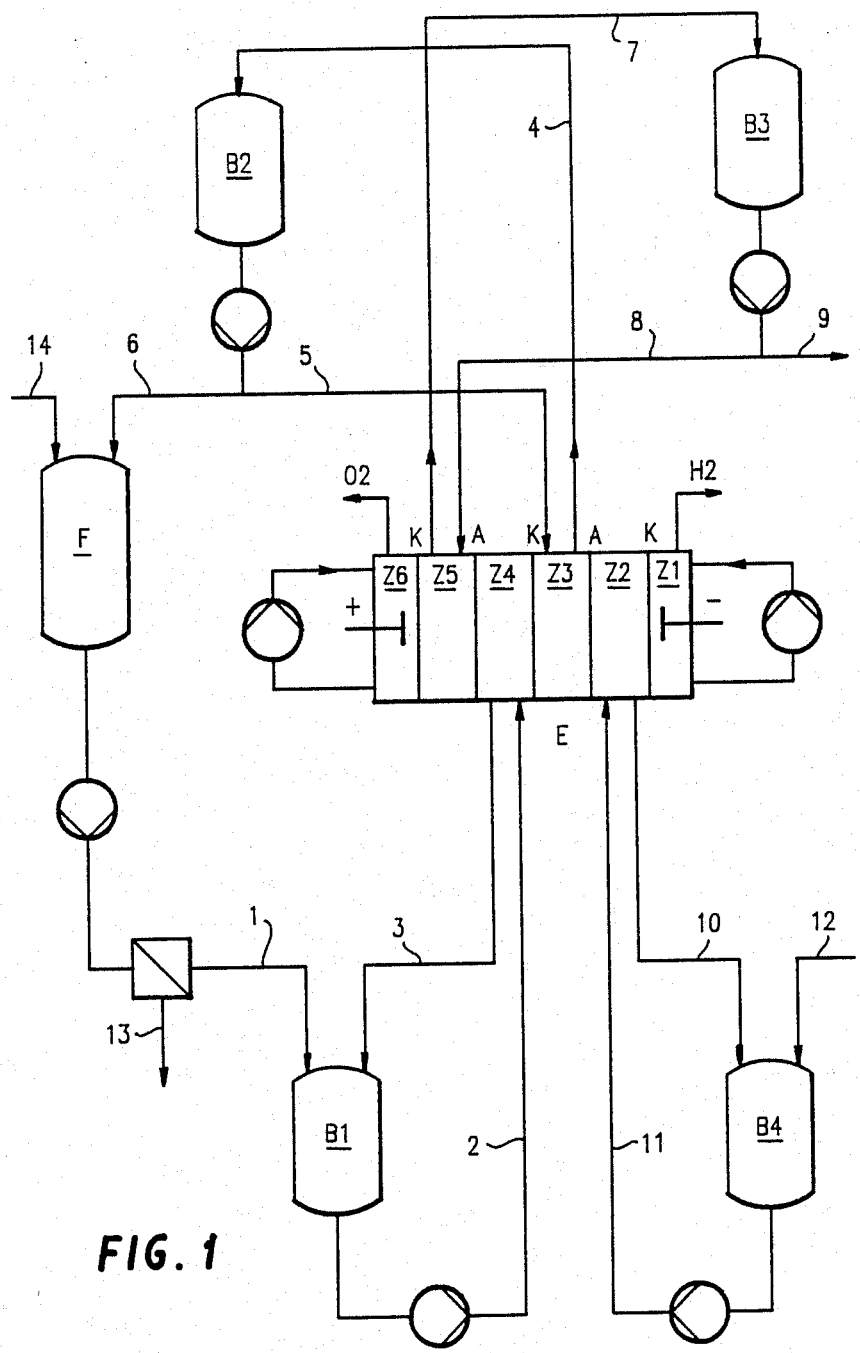
FIG. 1 shows an embodiment of a system for the fermentative preparation of L-malic acid and processing by electrodialysis.

The electrodialysis can be combined into one process with a fermentation. In these circumstances, to prepare L-malic acid, it is possible to convert, in aqueous solution, both fumaric acid into fumarate, which is fermentatively converted into malate, and also malate into L-malic acid. In this case, the two electrodialytic fumaric acid/fumarate and malate/L-malic acid conversions take place at the same time at 30° to 100° C. in the same electrodialysis equipment.

The sparingly water-soluble fumaric acid is preferably converted into a readily soluble alkali or ammonium fumarate which is used as the actual substrate for the fermentation. In the fermentation, the corresponding alkali or ammonium malate is then produced from the fumarate. In other cases the salt (BX) is supplied for a use other than fermentation.

The fermentation and electrodialysis can be performed continuously or batchwise. In the case of a batchwise procedure, intermediate containers are required for collecting the fumarate and malate solutions.

In a preferred embodiment the electrodialysis is performed in a row of 2 to 10 electrodialysis units. If one of the acids such as, for example, fumaric acid is sparingly soluble in water, the acid solution is passed through the electrodialysis units in parallel streams. The other solutions such as, for example, fumarate, malate and L-malic acid solutions, pass through the individual electrodialysis units consecutively in series.

The electrodialysis can be performed at various temperatures depending on the acids and salts used. The conversion of malate into L-malic acid is preferably performed, for example, at 50° to 60° C.

In these circumstances fumaric acid, fumarate, malate and L-malic acid solutions are circulated. In the batchwise procedure the electrodialysis is terminated when the L-malic acid solution contains 10 to 70% L-malic acid. In the continuous procedure an L-malic acid solution is circulated containing 10 to 70% L-malic acid. Pure L-malic acid can be prepared from the L-malic acid solutions by concentration, cooling and crystallization.

A special feature of the present invention is that a closed circuit is formed through the coupling of the substrate and product streams in the electrodialysis. The electrodialysis serves not only to liberate the organic acid in the processing stage, but also, if for example malate is prepared fermentatively from fumarate, to provide fumarate solutions for the fermentation at the outset. Surprisingly, the sparingly soluble fumaric acid can then be made available directly for the fermentation by means of electrodialysis. A preliminary reaction stage in which the fumaric acid is reacted with a hydroxide solution is not necessary.

In addition to hydroxide solutions, mineral acids (for liberating the organic acid) are also eliminated. Neither foreign substances nor waste waters are produced. Material losses are therefore very low.

The present process for extraction of organic acids may be applied to carboxylic acids, and to hydroxy-, amino- and ketocarboxylic acids containing 3 to 8 C atoms.

FIG. 1 shows as an embodiment, a system for the fermentative preparation of L-malic acid and the processing by electrodialysis. The electrodialysis unit E consists ot six cells made up of cathode and anode cells (Z1 and Z6) and four additional cells (Z2 to Z5) which are separated from each other by cation exchange membranes K or by anion exchange membranes A. A dilute sulfuric acid is passed through Z1 and Z6.

A fumaric acid solution is circulated through Z2 and container B4 and via the flow passages 10 and 11. An ammonium fumarate solution is circulated through Z3 and container B2 and via the flow passages 4 and 5. An ammonium malate solution is pumped through Z4 and container B1 and via the flow passages 3 and 2. An L-malic acid solution is passed through Z5 and container B3 and via the flow passages 7 and 8.

Fumaric acid and water are introduced via flow passage 12. L-malic acid is separated via flow passage 9.

Arrangements can also be chosen in which the cells Z2 to Z5 are repeated several times so that, on doubling, eight cells and two electrode cells are present and on a tripling, twelve cells and two electrode cells are present, and so on.

If the fermentation is operated batchwise, ammonium fumarate solution is passed from the stock container B2 into the fermenter F via flow passage 6. Cellular materials, nutrient solution and further auxiliary fermentation agents are introduced into the fermenter via flow passage 14.

The discharge from the fermenter consists of an ammonium malate solution which, after separation of the cellular materials (flow passage 13) is passed into the container B1 via flow passage 1 and collected there. The electrodialysis then also takes place batchwise independently of the fermentation with respect to time.

For continuous fermentation a continuous electrodialysis is performed. In this case ammonium fumarate is tapped off from the electrodialysis circuit for the fermentation via flow passage 6. Ammonium malate is fed into the circuit via flow passage 1.

When an electric field is applied, protons migrate in the electrodialysis unit from Z2 to Z1, fumarate ions from Z2 to Z3, ammonium ions from Z4 to Z3, malate ions from Z4 to Z5 and protons from Z6 to Z5. In this manner, L-malic acid is formed in Z5 and concentrated there.

L-malic acid is separated via the product flow passage 9. The fumaric acid impurities possibly produced during the concentration of the L-malic acid solution by evaporation may be returned to the process via flow passage 12.

Figure 2:
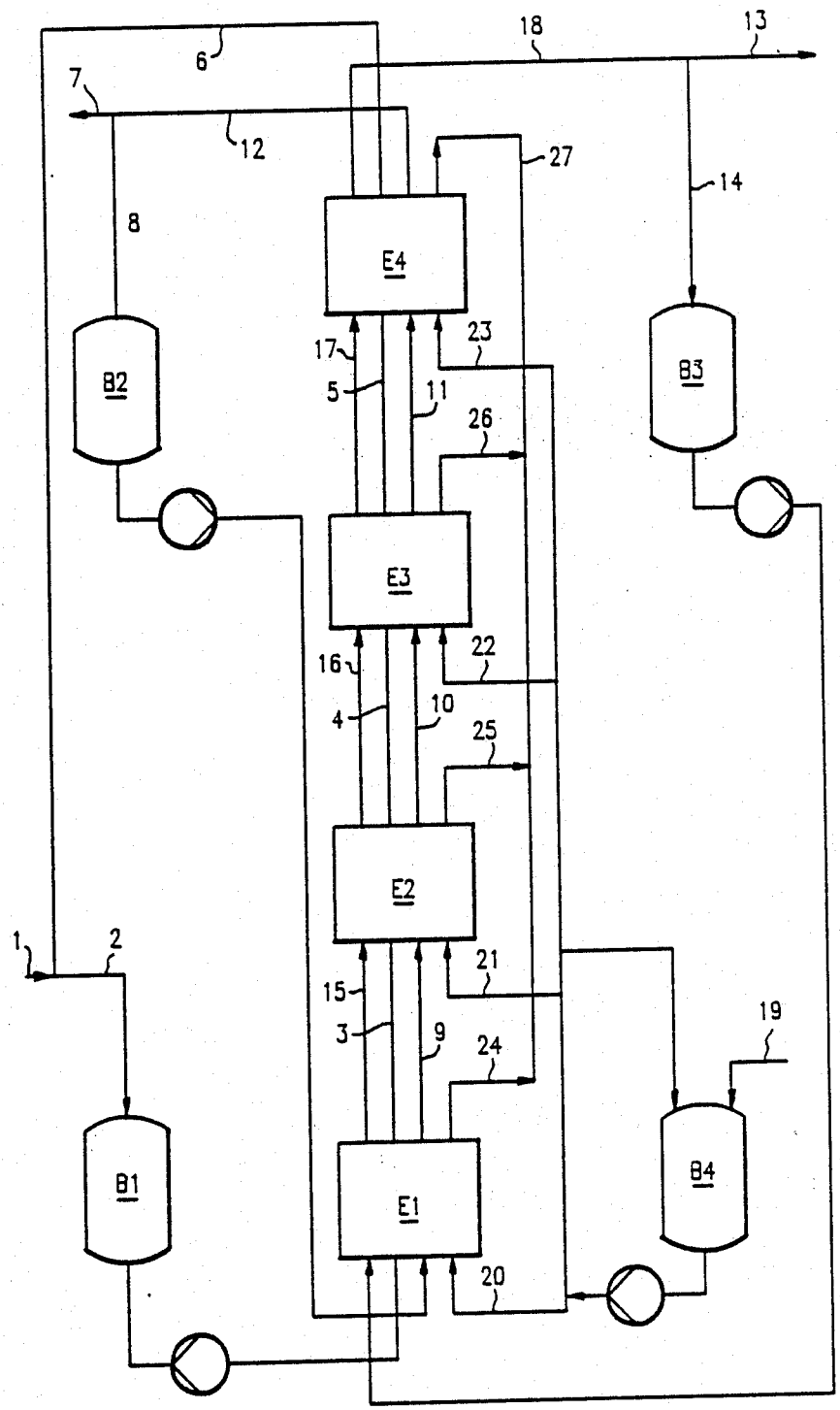
FIG. 2 shows an embodiment of the electrodialysis in four electrodialysis units.

FIG. 2 diagrammatically shows an embodiment in which the electrodialysis is performed in four electrodialysis units E1 to E4. Because of the low solubility of fumaric acid in water it is expedient to pass the fumaric acid solution from container B4 via four parallel flow passages 20, 21, 22 and 23 through the individual units. The solutions of ammonium fumarate (flow passages 9 to 12), ammonium malate (flow passages 3 to 6) and L-malic acid (flow passages 15 to 18) pass through the four units in sequence.

Fumaric acid is added via flow passage 19. Fumarate is fed to the fermenter via flow passage 7 and malate to the electrodialysis via flow passage 1.

L-malic acid is prepared from the product flow passage 13.

Other features of the invention will become apparent in the course of the following descriptions of exemplary embodiments which are given for illustration of the invention and are not intended to be limiting thereof.

EXAMPLES

Example 1

For the electrodialysis, use was made of an ammonium malate solution, free of cellular substance, which had been prepared from an ammonium fumarate solution by means of the fungus *Aspergillus wentii*.

The electrodialysis was performed in an electrodialysis unit containing 8 cells and 2 electrode chambers. The cation and anion exchange membranes were commercially available products based on styrene/divinylbenzene copolymers.

| Membrane area | 1 dm$^2$ |
|---|---|
| Thickness of the membrane | 0.2 mm |
| Distance between the membranes | 2 mm |

At the beginning of the experiment the following solutions were present:

| Electrode chambers: | 5% sulfuric acid | |
|---|---|---|
| Fumaric acid circuit: | fumaric acid | 80 g |
| | water | 3,815 g |
| Ammonium fumarate circuit: | water | 3,042 g |
| Ammonium malate circuit: | ammonium malate | 1,060 g |
| | ammonium fumarate | 150.4 g |
| | water | 3,262.7 g |
| L—malic acid circuit: | L—malic acid | 188 g |
| | fumaric acid | 2.5 g |
| | water | 1,079.5 g |

The elctrodialysis took place at 60°C. with a volumetric flow rate of 140 l/h in each circuit and a potential difference of 8V and a current of 1.05 to 1.25 A.

After 8 hours 40 g of fumaric acid was added to contained B4. The experiment lasted 12 hours in total. The funarate circuit contained 3.8% by weight of ammonium fumarate at the end of the experiment.

The product solution (L-malic acid circuit) had the following composition:

| L—malic acid | 246.4 g | 15% by weight |
| Fumaric acid | 19.4 g | 1.2% by weight |
| Ammonium malate | 0.3 g | 180 ppm by weight |
| Ammonium fumarate | 0.4 g | 240 ppm by weight |
| Water | 1,378.0 g | 83.8% by weight |

58.4 g Malic acid were prepared or 50.6 g of fumaric acid were converted. It was possible to prevent the formation of any succinic acid which could result from the reduction of the fumaric acid by hydrogen. The sulfur content was below 20 ppm.

On cooling the product solution to room temperature, crystals (92% by weight of fumaric acid, 8% by weight of L-malic acid) precipitated and were separated. 1,260 ml Water were then distilled off at 50 mbar and 50° C. On cooling the concentrated product solution to room temperature, crystals of the following composition were produced:

95.3% by weight L-malic acid
4.7% by weight fumaric acid

A further concentration of the mother liquor to dryness produced crystals having the composition:

98.3% by weight L-malic acid
1.7% by weight fumaric acid

Example 2

20% Ammonium aspartate solution prepared in a known manner (from ammonium fumarate by means of aspartase) was freed of high-molecular and colloidal particles by filtration and centrifuging. The solution was reacted with fumaric acid at 50° C. in accordance with Example 1. Because of the low solubility of the free aspartic acid the corresponding circuit was passed through a filter and the precipitating acid trapped. In this case, as in the subsequent examples, the same experimental apparatus was used as in Example 1. Initial concentrations were as follows:

Aspartate circuit: 1,012 g of ammonium aspartate 4,020 g of water and other substances
Fumarate circuit: 980 g of ammonium fumarate 3,870 g of water
Fumaric acid circuit: saturated fumaric acid (<2% by weight)
Aspartic acid circuit: water 55 g Aspartic acid were produced. Formation of 63 g of ammonium fumarate was correspondingly observed.

Example 3

Itaconic acid fermentatively prepared in a known manner (see U.S. Pat. No. 3,873,425) was first freed from interfering components as in Example 1 and converted into potassium itaconate by means of an ion exchanger. The potassium salt was then immediately reacted electrodialytically with sulfuric acid according to the process of the present invention:

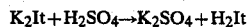

$$K_2It + H_2SO_4 \rightarrow K_2SO_4 + H_2It$$

(It = Itaconate)

In this example, a 4% potassium itaconate solution was reacted with 5% $H_2SO_4$. In addition to 86 g of $K_2SO_4$, 64 g of itaconic acid were produced from 104 g of potassium itaconate.

Example 4

A 10% sodium lactate solution was reacted at 30° C. according to the invention with a saturated solution of $CO_2$ in water (carbonic acid). 46 g Sodium lactate produced 36 g of lactic acid and 20 g of sodium carbonate which may be used as a solution for neutralizing and regulating the pH of a fermentation. A further purification of the lactic acid can be performed by known methods using ion exchangers, esterification or extraction.

Example 5

A 12% sodium tartrate solution was reacted at 30° C. according to the invention with 10% sulfuric acid. 65 g Tartaric acid were obtained from 85 g of sodium tartrate. In addition, 62 g of sodium sulfate were produced.

Example 6

90 g Sodium gluconate were reacted as a 12% solution with sulfuric acid as in Example 5, but at 60° C. In this case, 78 g of gluconic acid and the corresponding amount of sodium sulfate were produced.

Example 7

72 g Sodium glutamate were reacted as a 10% solution with sulfuric acid according to the invention as in Example 6 to produce 54 g of glutamic acid and the corresponding amount of sodium sulfate.

Example 8

85 g Sodium adipate were reacted as a 10% solution (after filtration as in Example 2) analogously to Example 6 with sulfuric acid to form 64 g of adipic acid and sodium sulfate.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A process of the preparation of a free organic acid, said acid comprising 3–8 carbon atoms, and 1–3 carboxyl groups, form a salt of the organic acid, comprising the steps of:
   converting said salt of the organic acid into said free organic acid by electrodialysis; and
   forming a second salt from the cation of said salt of the organic acid and the anion of a second acid;
   wherein said converting step and said forming step are performed in the same electrodialysis unit.

2. The process of claim 1, wherein said converting step is performed at about 30°–100° C.

3. The process of claim 2, wherein said converting step is performed at about 50°–60° C.

4. The process of claim 1, wherein said converting step is performed in 2–10 electrodialysis units and comprises:
   permitting the parallel flow of said second acid through said electrodialysis units and the consecutive flow of said free organic acid, salt of said organic acid, and said second salt through said electrodialysis units in series.

5. The process of claim 1, wherein said salt of the organic acid is prepared by batchwise fermentation and the electrodialysis is performed batchwise.

6. The process of claim 1, wherein said salt of the organic acid is prepared by continuous fermentation and the electrodialysis is performed continuously.

7. The process of claim 1, wherein said free organic acid further comprises at least one hydroxyl, amino or keto group.

8. The process of claim 1, wherein said free organic acid is a member selected from the group consisting of malic acid, aspartic acid, itaconic acid, lactic acid, tartaric acid, gluconic acid, glutamic acid and adipic acid.

9. The process of claim 1, wherein said second acid is fumaric acid, sulfuric acid or carbonic acid.

10. A process for the preparation of L-malic acid from a fermentatively prepared malate solution, comprising the steps of:

converting fermentatively prepared malate into L-malic acid by electrodialysis; and forming fumarate from fumaric acid by electrodialysis;

wherein said conversion and said formation steps are performed in the same electrodialysis unit at about 30°–100° C.

11. The process of claim 10, wherein said fumarate is an alkali or ammonium fumurate and wherein said malate is an alkali or ammonium malate.

12. The process of claim 10, wherein the electrodialysis is terminated when said L-malic acid solution contains about 10–70% L-malic acid.

* * * * *